United States Patent
Neubert et al.

(10) Patent No.: US 7,117,716 B2
(45) Date of Patent: Oct. 10, 2006

(54) DYNAMIC FRICTION TESTING VEHICLE TO MEASURE FLUID DRAG AND ROLLING FRICTION

(75) Inventors: Timothy W. Neubert, Tampa, FL (US); Barry Goff, Tampa, FL (US)

(73) Assignee: NAC Dynamics, LLC, Clearwater, FL (US)

( * ) Notice: Subject to any disclaimer, the term of this patent is extended or adjusted under 35 U.S.C. 154(b) by 0 days.

(21) Appl. No.: 11/196,664

(22) Filed: Aug. 3, 2005

(65) Prior Publication Data
US 2006/0144121 A1 Jul. 6, 2006

Related U.S. Application Data

(60) Provisional application No. 60/641,863, filed on Jan. 5, 2005.

(51) Int. Cl.
*G01N 19/02* (2006.01)
(52) U.S. Cl. ................................. 73/9; 73/7
(58) Field of Classification Search .................... 73/7, 73/9, 146
See application file for complete search history.

(56) References Cited

U.S. PATENT DOCUMENTS

| 3,301,039 | A | * | 1/1967 | Kummer | 73/9 |
| 4,130,008 | A | * | 12/1978 | Broshears | 73/9 |
| 4,662,211 | A | * | 5/1987 | Strong | 73/9 |
| 4,909,073 | A | * | 3/1990 | Takahashi et al. | 73/146 |
| 6,427,519 | B1 | * | 8/2002 | Ueda et al. | 73/9 |
| 6,463,784 | B1 | * | 10/2002 | Kashiwagi et al. | 73/9 |

* cited by examiner

*Primary Examiner*—Hezron Williams
*Assistant Examiner*—Ryan Christensen
(74) *Attorney, Agent, or Firm*—Dennis L. Cook, Esq.

(57) ABSTRACT

A portable Dynamic Testing Vehicle able to test for surface friction, drag, and travel distance, through contaminates accounting for longitudinal and lateral acceleration. The DFT is completely self contained with on board power supply, control unit, and water tank. The DFT has a high profile and long chassis to facilitate ease of movement and measurement at up to 100 km/h. Data obtained is transferred through the use of a wireless data transfer to a small handheld personal computer and then to a desktop computer where data is analyzed and or archived via specifically written software.

10 Claims, 5 Drawing Sheets

| < | > | | | | SAVE |
| 0006 | Program No. | 0 | Speed (km/h) | |
| ATLANTA | Airport Name | 0 | Test Distance (m) | REVIEW |
| ATLT | Designation | 0 | Offset | |
| MAIN MENU | | Runway No. | ☐ Water On | CANCEL |
| | ☐ Dual Run | 0 | Water Flow (lpm) | |

Figure 4b

| | Reset Readings | Turn Flashers ON | Remaing Storage (MB): 24.3 |
| EXIT | EVENT 1 | ZERO FLOW | Battery Status: Good |
| | | | Ambient Temp: 30660021 C |
| | | | START |

Friction       Speed          Distance

0.93 Mu simple  15 KPH  33 Meters

Figure 5

Example screen 5a

Example screen 5b

DYNAMIC FRICTION TESTING VEHICLE TO MEASURE FLUID DRAG AND ROLLING FRICTION

CROSS-REFERENCE TO RELATED APPLICATION

The present application claims the benefit of previously filed co-pending Provisional Patent Application, Ser. No. 60/641,863 filed Jan. 5, 2005.

FIELD OF INVENTION

This invention relates, generally, to a Dynamic Friction Tester (DFT) system and apparatus that is towed in order to quantify friction and drag characteristics of a surface such as roadway or runway for aircraft. More specifically, it is a 4 wheeled testing vehicle that provides real time data regarding friction and drag as adjusted for atmospheric conditions and contaminates present on the surface such as water, snow, ice, etc. that is stable at higher speeds and possesses extremely long run times with ease of calibration.

BACKGROUND OF THE INVENTION

Runway Friction Machines have been in existence since the early 1960's. Typically, these devices measure the resistance of a wheel to roll with regards to a runway, road, or other surface. This resistance will vary according to the friction characteristics of the surface tested. The introduction of water, snow, ice or other contaminates to the surface effects the accuracy of the data and makes the testing highly inaccurate. Accurate measurement of the surface is critical to braking protocols for vehicles that traverse said surface, for example, a pilot flying a commercial aircraft must know the proper coefficient of friction in order to brake appropriately upon landing. Machines presently available will give false information when measuring a runway with a contamination such as water, snow or slush. This additional rolling resistance will result in a friction machine recording a higher friction value when testing a contaminated runway, to the potential detriment to the vehicles traversing the surface.

In addition, a number of Friction Machines employ two wheels to generate the rolling friction value. This ultimately results in doubling of consumables as well as water quantity required. The Lock Wheel (variable Slip), employed on this product, employs a single friction measuring wheel, which reduces consumables.

In addition to the effect of contamination on aircraft braking performance, airfield operations in the wet depend on the depth of the water (contaminate) on the runway. This is because the impact of the water on the tire generates both a decelerating force on the tire and a spray that affects aircraft in terms of impingement on the airframe and ingestion by the engines. In conditions of snow or slush contamination, operations depend also on the strength properties of the contamination.

U.S. Pat. No. 4,098,111 by Hardmark et al. discloses a Roadway Friction Measuring Method and Apparatus for measuring and indicating limiting values for driving and braking vehicles in which a measuring wheel can be raised and lowered from a conventional wheeled vehicle to engage and disengage a substructure. Said wheel of this invention is driven within a predetermined slip in relation to vehicle speed and the resulting loads detected by suitably mounted transducers. Signals produced by the transducer are combined in an electric unit and displayed to indicate the braking force number. The apparatus of this invention is a single wheel device that measures the horizontal load in combination with the axle torque generated to calculate rolling friction. Therefore, this apparatus will not be able to distinguish between what is friction force and what is contamination force once said contamination is more than 3 millimeters deep.

U.S. Pat. No. 6,427,519 by Ueda et al. discloses a Road surface friction measuring method and device therefore wherein said device is mounted on a general car. The device has a spindle detachably connected to the wheel of a traveling wheel of a car, a support arm oscillatably connected to the spindle, and a measuring wheel supported rotatably by support arm. The support arm of this device contains vertical load generating mechanisms for applying a vertical load to be added to the self weight of the measuring wheel, a first detection unit for detecting the vertical load generating mechanism for applying a vertical load to be added to the self weight of the measuring wheel, a first detection unit for detecting the vertical load that is applied to the measuring wheel from the road surface, a rotation transmission mechanism for transmitting to the measuring wheel the rotation of the spindle so as to provide a circumferential velocity difference between the traveling wheel and the measuring wheel and a second detection unit for detecting the rotational resistance incurred by the measuring wheel from the road surface. The road surface friction coefficient is then calculated with a computing unit based on the self weight of the measuring vehicle including the detected values of these detection units and the arm itself.

Wherein Ueda et al's device does seem appropriate for the measurement of surface friction; there is no mention of rolling drag or lateral and longitudinal acceleration compensation. This would indicate that inaccuracies of measurements may be consistent in the data obtained from the device as disclosed in Ueda's patent.

Doherty discloses a vehicle mounted travel surface and weather condition monitoring system in U.S. Pat. No. 6,538,578 comprising of a system and apparatus for detecting and evaluating surface conditions on a road surface and atmospheric conditions simultaneously from a moving vehicle. The system comprises a sensor for detecting the presence of deposited material on a road surface, a detector for determining one or more characteristics of the deposited material such as its freezing temperature, process means for converting a detected signal and display means for displaying the condition of the road surface, and a sensor for detecting falling precipitation. An embodiment of the present invention includes a remote sensing apparatus which utilizes electromagnetic radiation to sense actual surface material conditions, temperatures, and composition and local atmospheric conditions at the vehicle as it is moving over a travel surface. This information is then processed through a computer in order to determine, preferably while the vehicle is in motion, those additional steps necessary to apply additional materials to the road surface in order to minimize hazardous driving conditions. Whereas this system and apparatus measures driving conditions, it has nothing to do with rolling friction or rolling drag measurement.

U.S. Pat. No. 4,662,211 by Strong discloses an apparatus for measuring friction characteristics of a vehicle-traveled surface comprising a wheeled vehicle having a test wheel assembly pivotally suspended there from by a parallelogram suspension arrangement. The test wheel assembly includes a test wheel carried by a drive shaft which is driven at predetermined slip by a differential coupled to the vehicle wheels. A gear chain extends from the differential to the drive shaft through a housing which forms one arm of the suspension. The second arm is formed by a rod which extends from the differential to one section of a two-axis strain gage wheel force transducer at the test wheel assembly. The differential is suspended by parallel struts from the vehicle frame. A positive displacement pump is coupled to the differential for placing a film of water beneath the test wheel having a thickness which is independent of vehicle speed. The pump and test wheel are clutch driven. Wherein the apparatus is seemingly appropriate for the measurement of surface characterizations, there is no mention of rolling friction or drag.

None of these apparatus describe a dynamic friction tester (DFT) that measures rolling friction, fluid drag, distance traveled, and normal load (vertical load on drag measuring wheel) while being mechanically suitable for Airport Operations.

Therefore, there is a need for such a system and apparatus for the dynamic and accurate and real time measurement of surface characteristics of surfaces such as roadways and runways.

It is an object therefore of this invention to provide a Dynamic Friction Tester (DFT) that may be towed behind a conventional vehicle.

It is another object of this invention to provide a DFT that measures rolling friction, fluid drag, normal load (vertical load of drag measurement wheel), and distance traveled.

It is another object of this invention to provide a DFT that is suitable for Airport Operations.

It is another object of this invention to provide a DFT with quick calibration procedures and the capability of full calibration including chassis geometry.

It is yet another object of this invention to provide a DFT that can measure single runs up to 10,000 meters and up to 500,000 total meters without needing replacement parts.

It is yet another object of this invention to provide a DFT that is dynamically stable when measuring at speeds up to 100 km/h.

It is yet another object of this invention to provide a DFT that is able to adjust friction reading against test speed, lateral accelerations, and longitudinal accelerations.

It is yet another object of this invention to provide a DFT with an independent power circuit.

It is yet another object of this invention to provide a DFT having a portable hand held data recording device with data analysis via specifically designed software readable on a customer desktop.

These and other objects of the invention will in part be obvious and will in part appear hereinafter.

BREIF DESCRIPTION OF THE FIGURES

The invention will be described, by way of example only, with reference to the accompanying figures in which.

Items of the Figures and Specification:
1. Overall Apparatus
2. Adjustable Tow Hitch
3. Nose Cone
4. Water Tank
5. Drag Sensor
6. Friction Sensor
7. On Board Battery Pack
8. On Board Battery Charger
9. Control Unit
10. Solar Panel
11. Distance Sensor
12. Drive Wheel
13. External Power Source
14. Rugged Hand Held Computer
15. Desk Top PC
16. Flexible Coupling
17. Load Cell

SUMMARY OF THE INVENTION

This invention relates to an apparatus and system comprising a Dynamic Friction Tester (DFT) that is meant to be towed behind a conventional vehicle in order to measure the rolling friction and rolling drag of a surface such as roadway or aircraft runway in a highly accurate fashion regardless of the environmental conditions or the presence of surface contaminants ambient to said surface and appropriate hardware and software to analyze and report the data.

A comprehensive modeling strategy for the decelerating forces generated by the motion of pneumatic tires through and all contaminants has been developed at the Engineering Science Data Unit (ESDU). Appropriate to this scheme, a second wheel on the DFT vehicle is instrumented to sense the forces generated by its passage through a contaminate. With suitable calibration, the output from the system is used to define either water depth or a combination of depth and physical properties of the snow through which the machine was traveling. The DFT rides upon 4 wheels and therefore is extremely stable. The DFT is fitted with two vertical load measuring sensors which detect lateral roll of the chassis and thus through suitable mathematics, the friction and drag readings are compensated against lateral accelerations. This enables the DFT to measure friction when accelerating, decelerating and negotiating corners. This extra-instrumented test vehicle provides for a more comprehensive model that can be created for calculating aircraft braking action on contaminated runways and high speed turn offs as being used on modern runways to increase traffic flow.

The DFT is equipped with a standard 2 inch or 50 millimeter fixed ball hitch. This primary tow hitch the Measuring tow hitch, is hinged to the DFT so tow vehicle oscillations are reduced. A secondary tow hitch may be provided lower on the DFT that affectively lifts the measuring wheels off the ground to facilitate movement of the apparatus eliminating any wear factors during non-measuring movement. In addition, the DFT may be reversed with no detrimental effect to the equipment. Many friction machines have a short wheel base and low profile and as such can be easily jack-knifed when reversed thereby resulting in expensive damage. Objects behind this vehicle remain clearly visible in the rear view mirror and the vehicle has a long chassis and tow bar facilitating reverse movement. The DFT is also fitted with an integrated water tank, eliminating the need for a second vehicle to store the water. This is possible because the DFT monitors vertical down load on to the measuring wheels and compensates the friction reading depending on vertical load as the water is being used.

The DFT uses a partial Locked Wheel (variable slip) that employs a single measuring wheel, thereby reducing consumable required. Friction is measured via a two axis load cell measuring horizontal and vertical deflections of the wheel axle. Fluid drag measurement uses a free rolling wheel with frictionless bearings. Resistance to rolling is the measured force at the wheel axle. Calibration of this wheel against test surfaces supplies zero drag readings. Contamination on the surface is then measured as an increase in axle deflection and conversely an ice surface will yield a decrease in axle deflection. This data is then correlated to give contaminate depth (equivalent water depth).

Distance traveled is measured using an electronic encoder fitted to the wheel axles to measure rotation and therefore distance traveled which is calculated to measure speed. Normal load is measured by the 2 axis load cell located on the axles. Equations have been written to calculate a contamination depth from the measured Normal (vertical) load. The entirety of the apparatus and system are mechanically suitable for airport operations. All fasteners are double secure. Aluminum may not be used due to the presence of de-icing fluids. Electronic measuring equipment may have stainless steel body construction with all electrical cables and sockets to be IP68 with an operating temperature range of −30+70 degrees Celsius. In addition, the DFT can measure single runs up to 10,000 meters. At runs, which are less than 1 km, full resolution is stored and displayed. As the run length increases there is an automatic decrease in the screen resolution. When greater than 1 km is required to be displayed on the screen the resolution of displayed readings is reduced by a factor of 10.

The DFT is stable when measuring at speeds up to 100 km/h. The standard towing speed for Airport Operations has been reduced over the years. In the 1990's the maximum test speed was 135 km/h. This has been reduced on safety grounds to 95 km/h and the UK CAA has reduced further its requirements to 65 km/h. The DFT has a total mass of 500 kg (not including the water system). The four wheel configuration and wide wheel base add to stability. Each wheel is fitted with full suspension shock and dampers. Friction devices vary the results when test speeds are changed. This is a function of dynamics and can be calculated out to give a single reading regardless of test speed or acceleration. This will eliminate the need to convert readings or consult charts against vehicle speed as shown in ICAO Annex 14. The final reading for the friction is displayed as Mu Ref. Friction readings are sensitive to lateral accelerations. The DFT is fitted with two vertical load measuring sensors which detect lateral roll of the chassis and thus through suitable mathematics, the friction and drag readings are compensated against lateral accelerations. This will become more useful as airport start to measure taxiways and high-speed runways turn-offs and will also be needed for highways measurements. The final reading for the friction will be displayed as Mu Ref. The DFT is fitted with two vertical load measuring sensors which when combined with the speed measuring system monitors for longitudinal acceleration. Using this, the friction readings (and drag) are compensated against acceleration/deceleration. This makes it possible to measure to the extremes of the runways. The final reading for the friction is displayed as Mu Ref.

To eliminate cables, the electronics are made independent to the tow vehicle. The DFT is fitted with Lead Acid Gel Filled Batteries to give 12V DC with 105 Amp capacity. This provides enough stored power to operate the DFT for over 350 Hours continuous operation. Charging of these batteries is through the integrated solar panels located on the nose cone of the DFT. This trickle charging of the batteries is continuous. The on board batteries can also be charged via an external 12V DC or 110–240V AC external supply.

Calibration of the system is critical to the operation and is quick and semi automatic. Calibration is performed immediately after the system is activated thereby eliminating the need for the operator to perform this function.

Data measured by the sensors fitted to the DFT vehicle are collated and processed by the on board Processor. The processor then converts the readings to actual Friction, Drag and Distance readings. These true readings are then sent to a Portable Hand Held computer. This computer will then record all the data in full resolution. Instantaneous readings are displayed on the Hand Held and then at the end of the survey the average readings are displayed. This gives quick and easy readings which can be sent to the control tower or flight office for immediate action. On return to the office the Hand Held is then "sinked" to the office computer which then down loads full resolution for full analysis.

Data analysis is via specific survey software installed in customers desktop computer and is compatible with Windows operating systems 98, 98SE, 2000, and XP.

DESCRIPTION OF THE PREFERRED EMBODIMENT

Figure 1:
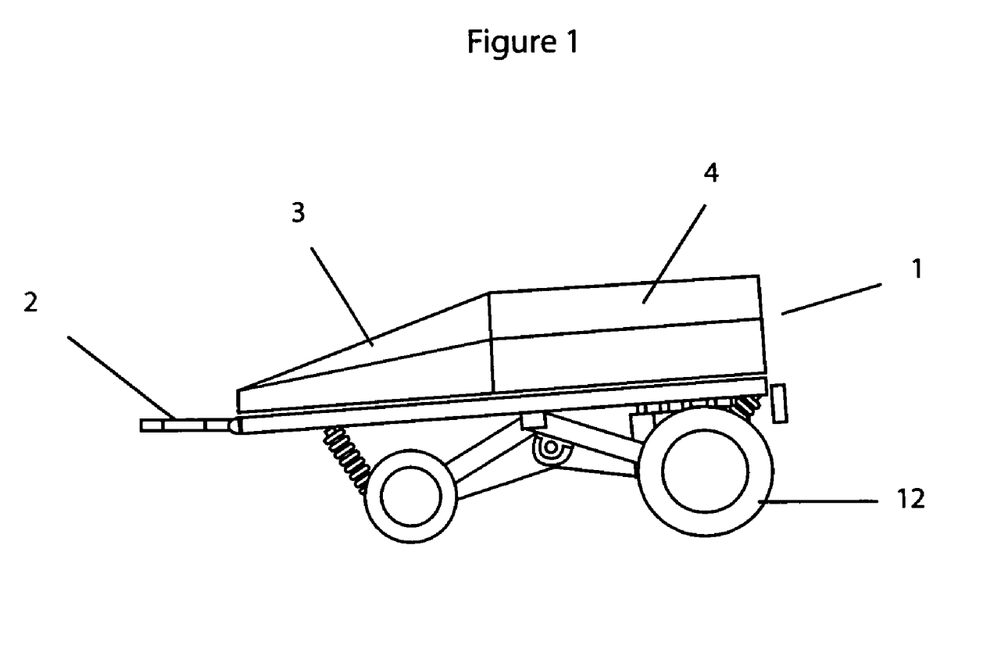
FIG. 1 shows a side view drawing of the overall assembly.

The present invention as shown in FIG. 1 is an apparatus comprised of the adjustable measuring tow hitch (2). A secondary non-measuring tow hitch (not shown) may be set below the measuring tow hitch (2) for non measurement towing. The nose cone (3) can contain a light bar (not shown) on its apex. Behind the nose cone (3) is located the water tank (4).

Figure 2:
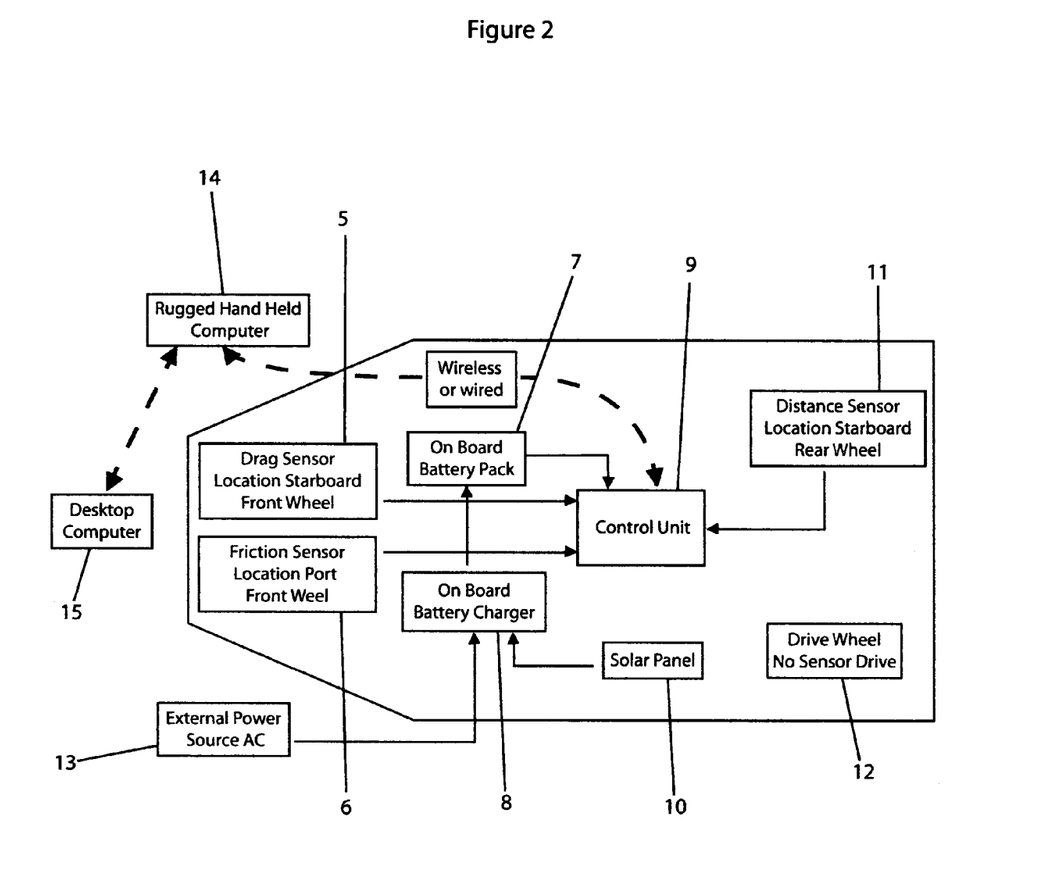
FIG. 2 is a block diagram showing each main component of the DFT.

FIG. 2 shows a schematic representation of the DFT from a top view. The front of the vehicle contains the drag sensor (5) wheel and the friction sensor (6) wheel. Data obtained by these two wheels is sent to the control unit (9) as is all information obtained by the distance sensor (11) wheel. The onboard battery pack (7) is connected to the onboard battery charger (8). In circuit with the battery charger (8) is a solar panel (10) or plurality of said panels that provides constant trickling current to the battery pack (7). The drive wheel (12) is not attached to the control unit (9). A distance encoder (11) is installed on the free rotating wheel at the starboard rear (not shown). Fitted directly to the axle, the resolution is recorded once every 35 millimeters, therefore 50 readings per one wheel rotation.

Figure 3:
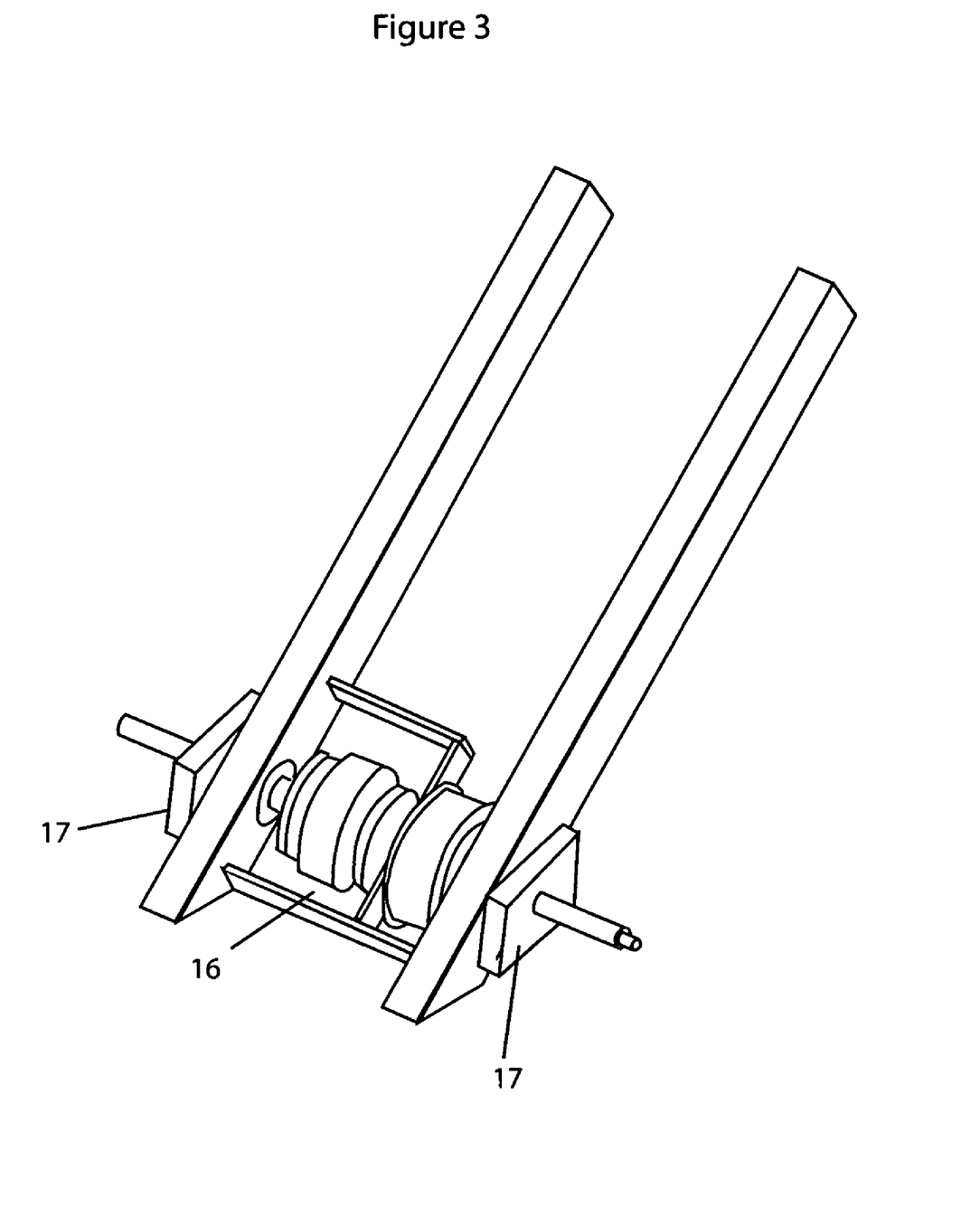
FIG. 3 is a perspective view drawing showing the front axle.

FIG. 3 is a representation of the front axle assembly of the apparatus. A load cell (17) is installed on the axle of both the friction sensor (6) and drag sensor (5) wheels. They are designed to measure forces in the two axis at 90 degrees. Drag and friction are measured in the X or horizontal plane and the normal force is measured in the Z or vertical plane. Force loadings are 5KN in the X and 10KN in the Z. An arrangement such as a flexible coupling (16) may be used in the font axle to account for variations in turning stress between the front measuring wheels.

Figures 4, 4A:
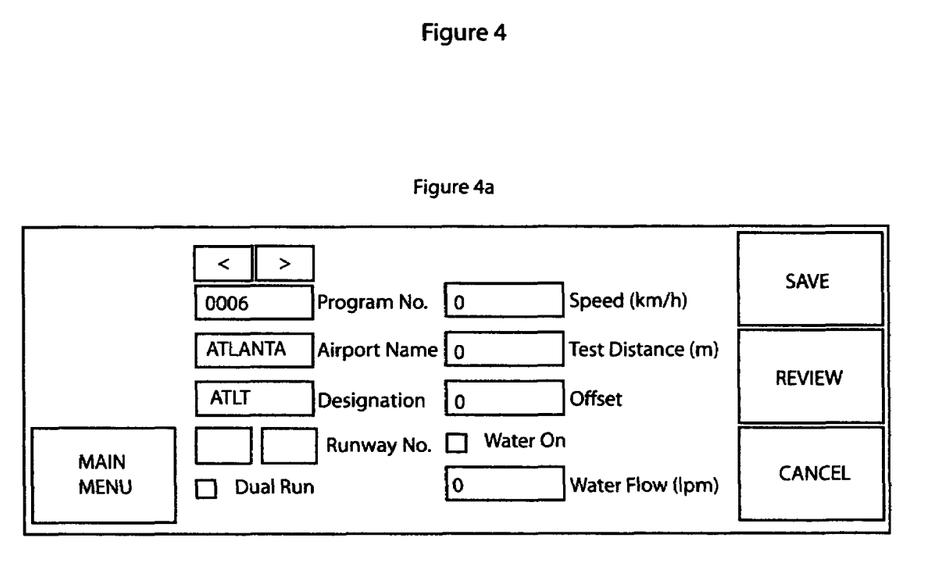
FIG. 4 is a representative data chart showing data as obtained and processed from the DFT using the specifically designed survey software.
Figure 4B:
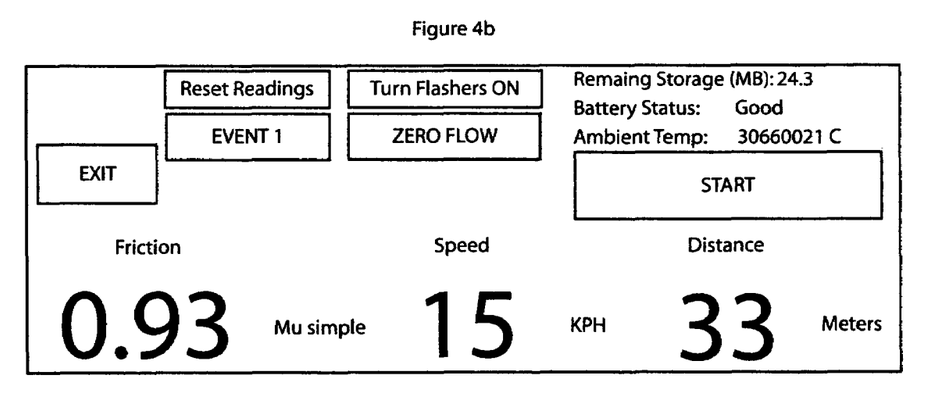

FIG. 4 shows an example screen 4*a* that is seen when using survey display software. After the information is "sinked" to the desktop computer (15) via standard USB or similar device, the data is interpreted by the software. Each survey is archived in a logical database as shown. The database can then be split in to the program fields. After selecting the surveys, the operator may select runs for comparisons that will be shown on a split screen as shown in example screen 4*b* of FIG. 4.

Figure 5:
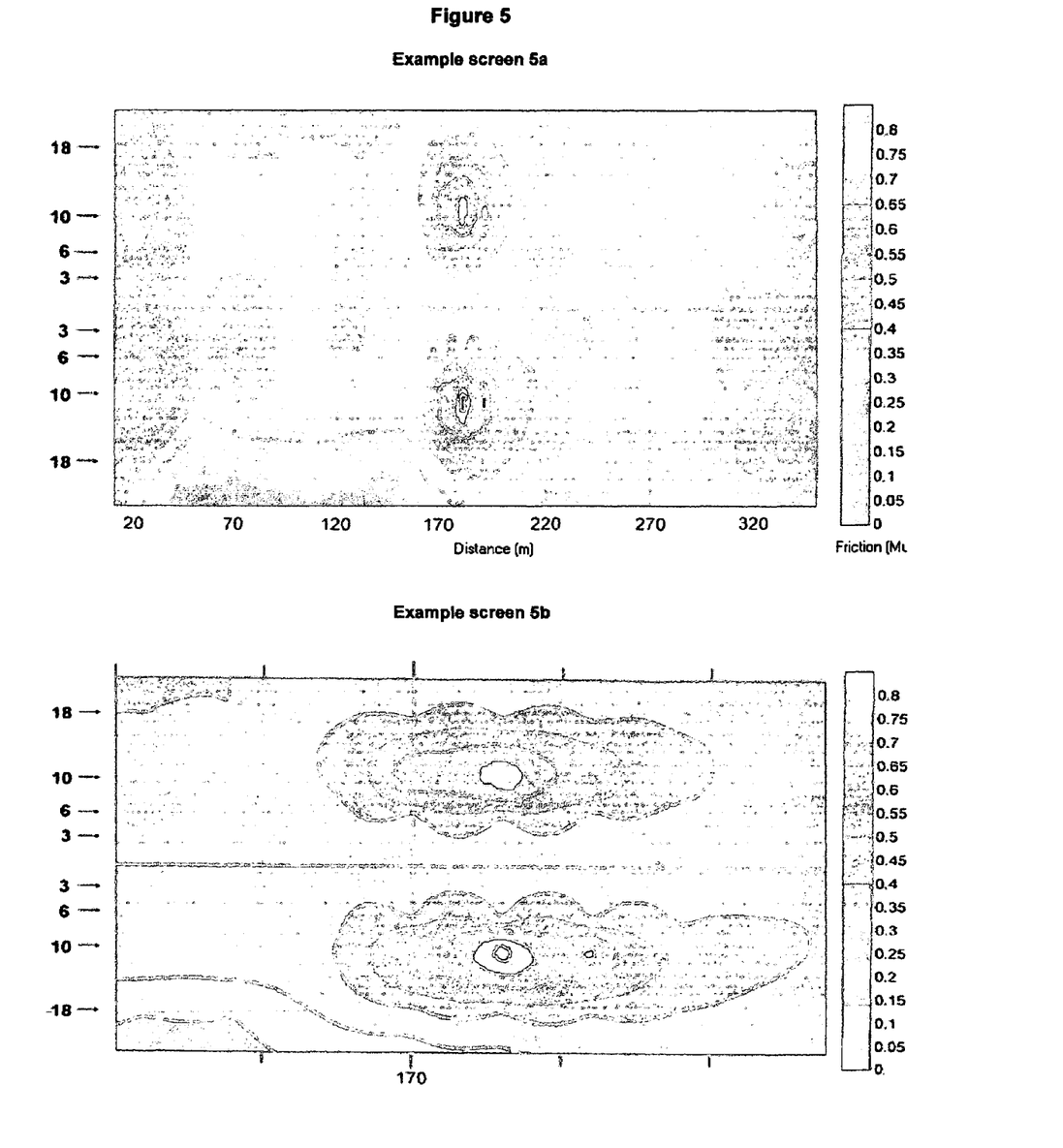
FIG. 5 is a representative data chart showing data as obtained and processed from the DFT using the specifically designed survey software.

FIG. 5 shows the data obtained as represented in a color scheme selected for either CAA CAP683, RCR, FAA or Full color image. Using the color range shows the lowest friction region in a red color and the highest friction in green as shown in example screen 5*a*. A zoom and pan function is available throughout the graphical screens and the ability to print any section of the survey as displayed is part of the system as shown in example screen 5*b*.

Further analysis of the surface tested can be performed by calculating the amount of surface that falls into specific friction levels. A software two dimensional plan view with defined friction values facilitates this action. Measurement of the forces generated by impact of fluid on the drag sensor (5) measuring wheel has shown to correlate with kinetic pressure and water depth. By inverting this correlation, water depth (contaminate depth) can therefore be inferred from the force measurement. Theoretical calculations for friction readings adjusted for lateral acceleration are used to compensate measured friction values against lateral acceleration of the test machine to equate Mu Ref values.

The specific survey software that computes the values and creates displays operates in accordance with the tables and equations shown in FIG. 6, and can be easily written by one skilled in the art. It is prudent to limit the operating speed to 40 ft/s because of the tendency of the measuring wheel to hydroplane at higher speeds in "deep" water. On the other hand, too low an operating speed will mean that the equipment will not be sufficiently sensitive to small depths of water. Of course, the operator is generally only concerned when depths are greater than one tenth of an inch.

Although this invention has been described in the form of a preferred embodiment, many modifications, additions, and deletions, may be made thereto without departure from the spirit and scope of the invention, a set forth in the following claims.

Mathematical Calculation for the DFT Software

DFT Equations

The equations will cover five separate DFT test conditions.
1. DFT Test—Dry Conditions
2. DFT Test—Wet and/or Slush Conditions
3. DFT Test—Ice Conditions
4. DFT Test—Snow Conditions
5. DFT Test—Simole (Non-ESDU) Test—All Conditions

Notation

As shown in ESDU Report, page xxxiii

Standard Data

As shown in ESDU Report, page xxxix
All data used in equations is in SI (Metric) Units.

1. DFT Test—Dry Conditions

Object

To evaluate the term $\mu_{REF}$ used in sections 6, 7, 8, 10, 11 of ESDU Report.

Required Measured Data.
Z Vertical force on Braked Wheel
Zr Vertical force on Free Wheel
Ftd Longitudinal force on Braked Wheel
Frdr Longitudinal force on Free Wheel
Pg Tire pressure (gauge)—assumed the same for both wheels.

V DFT speed
S Slip ratio
This test uses data from both test wheels.

The equation for $\mu_{REF}$ used the ESDU coefficients for $\eta_0$ and $\eta_1$.

The values obtained by ESDU for these coefficients were obtained for a wide range of vehicle and aircraft tires.

If a number of tests were to be performed on the DFT, at a later date, for a range of speeds and vertical loads, improved values of these coefficients could be derived for specific application to the DFT.

shows the equation for $\mu_{REF}$.

$$muRef := \frac{\left(1 + \frac{(.6842 + .00522426 s^2 V^2) p}{paZ^{1/3}}\right)\left(Ftd - Frdr\left(\frac{Z}{Zr}\right)^{(4/3)}\right)}{Z(1 - e^{(-12s)})}$$

2. DFT Test—Wet Conditions

Object

To evaluate the term d (depth of water or slush) used in sections 4, 5, 10, 11 of ESDU Report.

Required Measured Data.
Zr Vertical force on Free Wheel.
Frwr Longitudinal force on Free Wheel in the wet.
V DFT speed

Vehicle Data

Tire pressure (gauge).
w Tire width
D Tire Diameter

Other Data
pa Atmospheric pressure
σ Specific Gravity of Water, or Slush
ρ Density of Water.

This test uses data from the free test wheel only.

The required analysis for this test is complex at it will require the computational solution of the following cubic polynomial equation.

$$a_1.d^3 + a_2.d^2 + a_3.d + a_4 = 0$$

The solution to any cubic equation will yield 3 possible solutions.

In this case only the real positive solution has any meaning.

The other two meaningless solutions should be ignored. These two solutions will either comprise
2 negative real numbers, or
2 complex numbers containing imaginary parts.
Shows the equation for Wet Test depth.

$$a1 := 0.294056\, k\, p\, D^{(15/4)} \cos(\theta)^4$$

$$a2 := kp\cos(\theta)^4 w\left(.235245 D^{(15/4)} w + .047049 D^{(15/4)} - .180064 D^{(23/4)} w\right) + \\ 6.555 kp w^4 (1 + \sin(\theta)) + 2.15278 p\sigma D^3 w^3 (pZr)^5 \ln\left(\frac{1}{\sigma}\right)$$

$$a3 := w^5 D^3 \sigma p (pZr)^5 \ln\left(\frac{1}{\sigma}\right)(1.72222 - 1.31825 D^2) + \\ kp w^3 \cos(\theta)^4 \left(.0376392 D^{(15/4)} - .0288103 D^{(23/4)}\right) +$$

-continued $$kpw^6(1+\sin(\theta))(5.244-4.01393D^2)+$$
$$D^2w^2Zr^{(4/3)}(.237928V^2+381.891)-$$
$$FrwrpD^2w^2+.0176375kpw^3D^2\cos(\theta)^2(1-\sin(\theta))$$

In $$a4:=-Zr^{(4/3)}D^2w^4(0.145695\ D^2V^2-305.513+233.85$$
$$D^2-0.190342\ V^2)-Frwr\ p\ D^2w^4(0.8-0.612347$$
$$D^2)$$

$q=0.5.\sigma.\rho.V^2$ $\theta=\tan^{-1}(1-q/p)$

Possible Computational Problem

During the calculation of the water/slush depth 'd', indirect use is made of the ESDU Renort equation for the calculation of the force acting on the free rotating wheel during dry conditions, because this quantity cannot be measured during a wet test.

This dry force Frdr is given by:

$$Frdr=(3.7699*10^{-3}+2.34875*10^{-6}*V^2)*(pa*Zr^{4/3}/p)$$

However, this equation is not exact and, as yet, its accuracy with respect to the DFT has not been verified.

When attempting to evaluate the depth of contaminant, use is made of the difference between this theoretical dry force and the measured longitudinal force Frwr that acts on the free rolling wheel during wet conditions. Under conditions of very low values of water depth this difference will also be very small.

Hence, any small error in the theoretical value of Frdr above, could lead to Frdr being apparently marginally higher than Frwr, instead of marginally lower. This will lead to an instability in the calculation of 'd'.

To prevent this, at each sampling stage the computation should initially check to detect if Frdr exceeds Frwr. This should be performed before attempting to evaluate the water depth 'd'.

Whenever this condition is seen to occur, the computation should avoid attempting to calculate the water depth, and the program should simply report that the water/slush depth is too small to evaluate, or is even zero.

3. DFT Test—Ice Conditions

Object

To evaluate the term $\mu_{REF\ ICE}$ used in section 12 of ESDU Report.

Required Measured Data.

Z Vertical force on Braked Wheel
Zr Vertical force on Free Wheel
Fti Longitudinal force on Braked Wheel
Frir Longitudinal force on Free Wheel
Pg Tire pressure (gauge)—assumed the same for both wheels.
V DFT sneed
s Slip ratio This test uses data from both test wheels.

The equation for $\mu_{REF\ ICE}$ used the ESDU coefficients for $\eta_0$ and $\eta_1$.

The values obtained by ESDU for these coefficients were obtained for a wide range of vehicle and aircraft tires.

If a number of tests were to be performed on the DFT, at a later date, for a range of speeds and vertical loads, improved values of these coefficients could be derived for specific application to the DFT.

shows the equation for $\mu_{REF\ ICE}$ $$muRefice := \frac{\left(Fti - Frir\left(\frac{Z}{Zr}\right)^{(4/3)}\right)\left(1 + \frac{(.6842 + .005224260960s^2V^2)(pg+pa)}{paZ^{1/3}}\right)}{(1-e^{(\eta 2s)})Z}$$

$$\eta 2 := -12 \cdot \frac{pa(4.pa+7.\rho s^2V^2)}{(2.pa+\rho s^2V^2)^2}$$

Also shown is the required equation $\eta_2$

Note that pa is the atmospheric pressure in N/m²

4. DFT Test—Snow Conditions

Object

To evaluate the term $d_{snow}$ (i.e. d, depth of snow) used in sections 5, 12 of ESDU Report.

To evaluate the term $\mu_{REF\ ICE}$ used in section 12 of ESDU Report.

Required Measured Data.

Z Vertical force on Braked Wheel
Zr Vertical force on Free Wheel
Fts Longitudinal force on Braked Wheel in snow
Frsr Longitudinal force on Free Wheel in snow
Pg Tire pressure (gauge)—assumed the same for both wheels.
V DFT speed
s Slip ratio This test uses data from both test wheels.

The equation for $\mu_{REF\ ICE}$ used the ESDU coefficients for $\eta_0$ and $\eta_1$.

The values obtained by ESDU for these coefficients were obtained for a wide range of vehicle and aircraft tires.

If a number of tests were to be performed on the DFT, at a later date, for a range of speeds and vertical loads, improved values of these coefficients could be derived for specific application to the DFT.

Shows the equation for $d_{snow}$ $$dsnow := \frac{D\left(\frac{Frsr-Frdr}{kl}\right)^{(3/4)}}{Rvoid}$$

$$kl := \frac{OEsnow\ GsZr\left(1+\frac{sigmaSnow\rho V^2}{Cu}\right)^{(1/4)}}{pg+pa}$$

-continued $$Frdr := \frac{(.0037699 + .234874617810^{-5}V^2)Zr^{(4/3)}pa}{pg + pa}$$

Rvoid:=1−1.086956522 sigmaSnow
Cu:=0.2681310$^7$ e$^{(-13.82\ Rvoid^{2.5})}$
Gs:=0.3497710$^{10}$ e$^{(-13.82\ Rvoid^{1.5})}$ Shows the equations for $\mu_{REF\ ICE}$ $$muRefice := \frac{(Fts - Frs)k3}{k2}$$

$$Frs := Frdr\left(\frac{Z}{Zr}\right)^{(4/3)} + \frac{GsnowrZ}{Zr}$$

$$k2 := (1 - e^{(\eta 2s)})Z$$

$$k3 := 1 + \frac{(.6842 + .005224260960s^2V^2)(pg + pa)}{paZ^{1/3}}$$

$Gsnowr :=$ $$\frac{OEsnow\ Gs\ Zr\left(\frac{(1 - 1.086956522\ sigmaSnow)\ dSnow}{D}\right)^{(4/3)}\left(1 + \frac{sigmaSnow\rho V^2}{Cu}\right)^{(1/4)}}{pg + pa}$$

$$\eta 2 := -12.\frac{pa(4.pa + 7.\rho s^2 V^2)}{(2.pa + \rho s^2 V^2)^2}$$

Also shown in each file are the required sub-equations.

Other Data

The parameter OEsnow represents the EDSU term O[Gsnow]/E[Gnsow].

Values are suggested on page xli in the ESDU Report.

During sample runs of these equations a value QEsnow=1, has been chosen.

However, other values may be utilized in the presented equations if desired.

The parameter sigmaSnow is specific gravity of snow. See ESDU Report. Table 5.2.

Note that pa is the atmospheric pressure in N/m$^2$.

5. DFT Test—Simple (Non-ESDU) Test—All Conditions

Object

To evaluate the following simple (non-ESDU) terms:
(i) $\mu_{ROLL}$
(ii) $\mu_{SLIP}$ Such that:

$F_R = \mu_{ROLL} * Z_R$ and $F = (\mu_{ROLL} + \mu_{SLIP}) * Z$

Where

Z Vertical force on Braked Wheel
$Z_R$ Vertical force on Free Wheel
F Long. force on Braked Wheel (includes rolling, contaminant and slip effects)
$F_R$ Long. force on Free Wheel (includes rolling and contaminant effects only)

$\mu_{ROLL}$ Refers to rolling and contaminant effects only.
$\mu_{SLIP}$ Refers to slip effects only.

Required Measured Data.

Z Vertical force on Braked Wheel
$Z_R$ Vertical force on Free Wheel
F Long. force on Braked Wheel (includes rolling, contaminant and slip effects)
$F_R$ Long. force on Free Weel (includes rolling, contaminant effects only)

V DFT speed—but not used in calculation
S Slip ratio—but not used in calculation This test uses data from both test wheels.

Equations $\mu_{ROLL} = (F_R/Z_R)$ $\mu_{SLIP} = (F/Z) - (F_R/Z_R)$

Note

These simplified values of $\mu_{ROLL}$ and $\mu_{SLIP}$ may not be applicable to other test conditions, such as other wheel sizes, vertical loads, speeds and slip values.

The Total Effective Coefficient of Friction $\mu$ can be obtained by the addition of the above two components as follows.

$\mu = \mu_{ROLL} + \mu_{SLIP}$

What is claimed is:

1. A testing system meant to be towed behind a conventional vehicle in order to measure the rolling friction and rolling drag of a surface such as roadway or aircraft runway regardless of lateral acceleration or deceleration, environmental conditions, or the presence of surface contaminants ambient to said surface comprising:

A vehicle capable of being towed;
Said vehicle having a drag sensor wheel, a friction sensor wheel, a distance sensor wheel, and a drive wheel connected to said vehicle and arranged such that said drag sensor wheel, friction sensor wheel, distance sensor wheel, and drive wheel the touch a surface to be tested and rotate as said vehicle is towed over the surface;

said drag sensor wheel and said friction sensor wheel each having 2-axis load cells for sensing loads in both a horizontal and a vertical direction;

said distance sensor wheel capable of measuring distance towed over the surface;

a 2-axis accelerometer located on said vehicle;

a power source located on said vehicle;

a control unit located on said vehicle;

a data storage unit;

said control unit electrically connected to each of said 2-axis load cells, said distance wheel sensor, said 2-axis accelerometer, and said power source; and, said control unit capable of processing data from each of said 2-axis load cells, said 2-axis accelerometer, and said distance wheel sensor to compute surface distance, drag and friction values in real time and capable of transferring said surface distance, drag and friction values to said data storage unit.

2. The testing system of claim 1 further comprising a water tank located on the vehicle for wetting the surface to be tested.

3. The testing system of claim 1 wherein said power source is a battery pack.

4. The testing system of claim 3 wherein said battery pack is capable of being recharged.

5. The testing system of claim 4 further comprising solar cells to recharge said battery pack.

6. The testing system of claim 1 wherein said data storage unit is a portable hand held computer.

7. The testing system of claim 6 wherein said portable hand held computer is capable of graphically displaying said stored values.

8. The testing system of claim 1 wherein said data storage unit is a desktop computer.

9. The testing system of claim 8 wherein said desktop computer is capable of graphically displaying said stored values.

10. The testing system of claim 1 wherein said control unit is capable of computing surface distance, drag and friction values in real time while compensating for lateral acceleration or deceleration based on data received from said 2-axis load cells.

* * * * *